(12) United States Patent
Rhoades

(10) Patent No.: US 6,652,888 B2
(45) Date of Patent: *Nov. 25, 2003

(54) METHOD FOR SKIN REJUVENATION WITH BUFFING CREAM

(75) Inventor: Dean L. Rhoades, Los Angeles, CA (US)

(73) Assignee: Dermanew, Inc., Beverly Hills, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/411,712

(22) Filed: Oct. 4, 1999

(65) Prior Publication Data

US 2001/0046506 A1 Nov. 29, 2001

(51) Int. Cl.⁷ .......................... A61K 33/08; A61K 7/00; A61K 7/48; A61B 17/50; A61M 35/00; C09K 3/14

(52) U.S. Cl. .................. 424/691; 15/244.1; 51/309; 424/401; 601/46; 604/289; 604/290; 606/131

(58) Field of Search .......................... 424/401; 51/307, 51/309; 601/46, 89, 97, 112; 606/131; 15/244.1; D28/7; 604/289, 290

(56) References Cited

U.S. PATENT DOCUMENTS

| | | | | |
|---|---|---|---|---|
| 3,092,111 A | * | 6/1963 | Saperstein | ................ 606/131 |
| 4,284,533 A | | 8/1981 | Imamura et al. | ............. 510/398 |
| 4,344,930 A | * | 8/1982 | MacRae et al. | .............. 424/401 |
| 4,957,747 A | | 9/1990 | Stiefel | ........................ 424/401 |
| 4,992,476 A | | 2/1991 | Geria | ......................... 514/782 |
| 5,360,824 A | | 11/1994 | Barker | ....................... 424/680 |
| 5,679,877 A | | 10/1997 | Erilli et al. | .................. 510/218 |
| 5,753,245 A | | 5/1998 | Fowler et al. | ............... 424/401 |
| 5,800,446 A | | 9/1998 | Banuchi | ..................... 606/131 |
| 5,891,449 A | | 4/1999 | Daniel et al. | ................ 424/401 |
| 6,090,085 A | | 7/2000 | Mehl, St. et al. | ............ 604/291 |
| 6,139,553 A | | 10/2000 | Dotan | ........................ 606/131 |
| 6,290,976 B1 | | 9/2001 | Messenger | .................. 424/401 |

FOREIGN PATENT DOCUMENTS

| | | |
|---|---|---|
| DE | 27 18 158 A | 11/1978 |
| EP | 0 336 900 A | 10/1989 |
| EP | 0 571 193 A | 11/1993 |
| FR | 2 564 318 A | 11/1985 |
| GB | 1 021 276 A | 3/1996 |
| WO | WO 92 21306 A | 12/1992 |
| WO | WO 99/21532 | * 5/1999 |

* cited by examiner

*Primary Examiner*—John Pak
*Assistant Examiner*—Frank Choi
(74) *Attorney, Agent, or Firm*—Blakely, Sokoloff, Taylor & Zafman LLP

(57) ABSTRACT

A cream moisturizer for resurfacing human skin is provided with a suspension of microcrystals of alumina ($Al_2O_3$) in a ratio of approximately 14 grams per ounce of moisturizer cream. The cream moisturizer is buffed into the epidermal layer of the skin with a closed-cell sponge pad driven by a vibrator. The alumina microcrystals buffs an epidermal layer off the skin to provide a soft smooth surface, thereby rejuvenating the skin.

10 Claims, 1 Drawing Sheet

METHOD FOR SKIN REJUVENATION WITH BUFFING CREAM

FIELD OF THE INVENTION

The invention relates to the art of skin treatment for rejuvenation without chemical or laser peels, but nevertheless resurfacing the skin to improve its soft youthful appearance.

BACKGROUND OF THE INVENTION

Facial skin rejuvenation has been accomplished by chemical treatment referred to as "chemical peels" or laser treatment referred to as "laser surgery" and exfoliation by machine driven means, such as with emery paper. Such methods require medical supervision and involve some risk of deleterious side effects as well as pain and discomfort during treatment. These methods all require long recovery time between treatments.

What is desired is an inexpensive method that may be safely applied upon ones own skin as often as necessary or desired to achieve and retain the desired rejuvenation without pain or discomfort during treatment and absolutely no recovery time.

SUMMARY OF THE INVENTION

A method is disclosed. In one embodiment, the method includes buffing an area of human skin with a cream moisturizer having microcrystals of alumina suspended therein. The area of human skin is buffed using a sponge massaging pad on the head of a vibrator.

In accordance with the present invention, a cream moisturizer having approximately fourteen grams of alumina ($Al_2O_3$) microcrystals dispersed per ounce of cream for microderm abrasion is applied to the skin to be treated by using a closed cell sponge buff-pad secured to a hand-held electric vibrator. By running the vibrator-driven buff-pad over the cream, the alumina microcrystals dispersed in the cream buffs off an epidermal layer the skin, thereby leaving a fresh soft epidermis, all without any pain or discomfort. Meanwhile, the cream moisturizes the new epidermis while also treating it with beneficial vitamins from the ingredients of the cream mixture, such as vitamins A and C.

The novel features that are considered characteristic of this invention are set forth with particularity in the appended claims. The invention will best be understood from the following description when read in connection with the accompanying drawings.

DETAILED DESCRIPTION OF THE INVENTION

Figure 1:
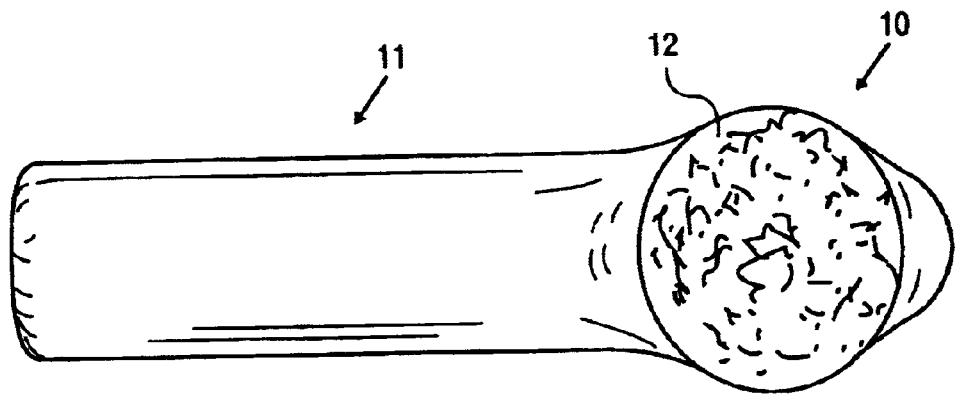
FIG. 1 is a plan view of a conventional hand-held electrical massaging vibrator having a snap-on disk with a closed-cell sponge buff-pad on the massaging head thereof.
Figure 2:
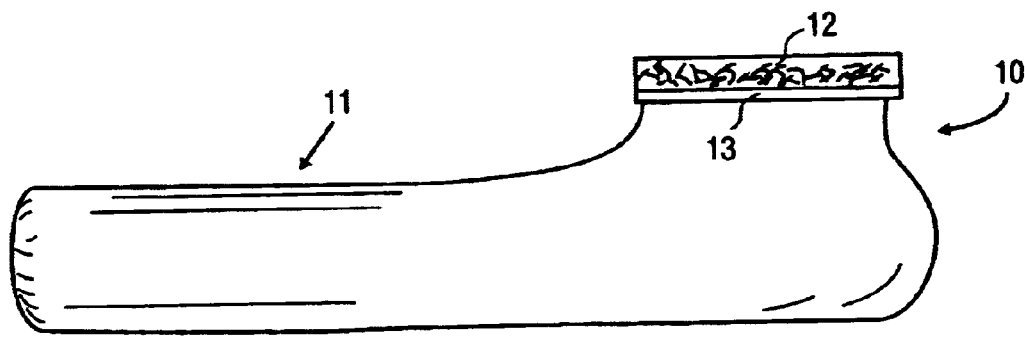
FIG. 2 is a side view of the massaging vibrator of FIG. 1.

Referring to FIGS. 1 and 2, a conventional electric (dc battery or ac power driven) vibrator is encased in housing having a head portion 10 and a handle 11 which houses AA batteries in the case of a DC driven vibrator. The vibrator is used for massaging a person's skin using a sponge buff-pad 12 secured to a cap 13 as shown in FIG. 2. The buffer pad is preferably made of polyurethane, but any closed-cell sponge material may be used for the pad. The cap which snaps onto the head portion is replaceable.

Figure 3:
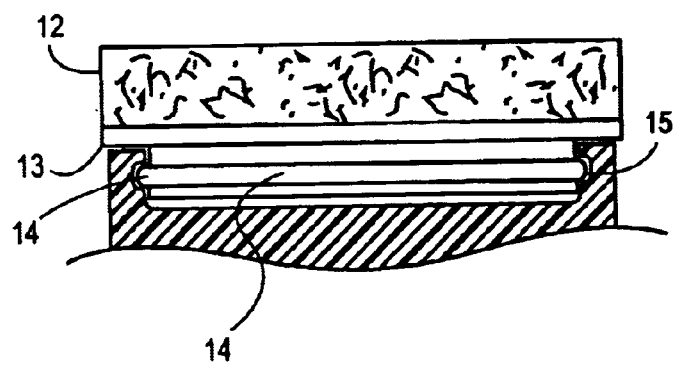
FIG. 3 shows to a larger scale a portion of the massaging head in cross section and a side view of the snap-on disk (on which the closed cell sponge buff-pad is secured) snapped into place on the head portion.

Referring to FIG. 3, the manner in which the cap snaps onto the head portion 10 is shown. A ridge 14 around the outer wall of the cap 13 snaps into a groove 15 around the inside wall of the head portion 10 to securely hold the cap in place. Alternatively, the cap may have a groove that snaps over a ridge around the inside wall of the head. The sponge pad 12, which is secured to the top of the cap 13 with an adhesive, is intended to be replaced after many uses.

A jar for the cream moisturizer (not shown) should have a mouth large enough for the sponge pad 12 to be dipped into the cream before or after snapping it on the vibrator. Alternatively, the cream may be scooped out of the jar by hand and applied to the skin area to be treated. In either case, the vibrator is turned on and moved about the area of the skin to be treated with the cream moisturizer until the cream has been worked into the skin and the resurfaced epidermis appears soft and smooth.

The alumina crystals suspended in the cream moisturizer provide gentle microdermabrasion of the skin for resurfacing the skin, leaving it smooth and soft after each treatment without the need of any recovery time so that it may be repeated as often as on a daily basis, in order to reduce and erase fine lines and wrinkles, reduce pore size, reduce or erase sun damage, age spots and skin discoloration firm skin and muscle tone, thereby to reduce sagging, enhance new epidermal cells and decongest acne skin conditions. This method of rejuvenating the skin, and particularly the facial skin, is ideal for those unwilling or unable to undergo laser surgery, a chemical peel, or machine driven exfoliation.

The ingredients of a preferred cream moisturizer includes:

14 GRAMS OF ALUMINUM OXIDE CRYSTALS (ALUMINA) $AL_2O_3$
PER 1 OUNCE OF CREME
VITAMIN A
WATER
WHEAT (*TRITICUM VULGARE*)
GERM OIL/CAPRIC TRIGLYCERIDE
CATARRHAL ALCOHOL
TOCOPHEROL
BEMZOPHENONE-3
SODIUM CATARRHAL SULFATE
CARROT (*DAUCUS CAROTA*) EXTRACT
PEANUT (*ARACHIS HYPOGAEA*) OIL
ISOPROPYL MYRISTATE
PROPYLENE GLYCOL
WHEAT (*TRITICUM VULGARE*) GERM EXTRACT
WHEAT (*TRITICUM VULGARE*) BRAN EXTRACT
SORBIC ACID
RETINYL PALMITATE
DEHYDROACETIC ACID
METHYLPARBEN
ASCORBYL PALMITATE
AMINOMETHYL PROPANOL
PROPTLPARABEN
CITRIC ACID
PANTHENOL
LECITHIN

Other formulations of a cream moisturizer may occur to those skilled in the art which, upon suspending alumina microcrystals in the cream in accordance with the present invention, would be within the scope of the following claims.

What is claimed is:

1. A method for rejuvenating the human skin with a cream moisturizer having suspended microcrystals of alumina therein, the method comprising buffing an area of the skin with the cream moisturizer using a sponge massaging pad on the head of a vibrator, wherein the microcrystals of alumina are present in an amount in the cream moisturizer effective to resurface the human skin.

2. The method of claim 1, wherein the microcrystals of alumina are suspended in the cream moisturizer in a ratio of approximately 14 grams per ounce of cream moisturizer.

3. The method of claim 1, wherein the sponge massaging pad is disposable.

4. A method comprising:
   applying to an area of skin a composition comprising a moisturizer and an effective amount of microcrystals of alumina to, in the presence of a vibrating instrument comprising a sponge disposed on the vibrating instrument, remove a layer of human skin; and
   vibrating the area of skin.

5. The method of claim 4, wherein the composition comprises 14 grams of alumina per ounce of cream.

6. A method comprising:
   applying to an area of skin a composition comprising a moisturizer and an effective amount of microcrystals of alumina to, in the presence of a vibrating instrument comprising a sponge disposed on the vibrating instrument, remove a layer of human skin; and
   massaging the area of skin.

7. The method of claim 6, wherein the composition comprises 14 grams of alumina per ounce of cream.

8. A method comprising:
   applying to an area of skin a composition comprising a moisturizer and an effective amount of microcrystals of alumina to, in the presence of a vibrating instrument having a sponge disposed on the vibrating instrument, remove a layer of human skin; and
   abrading the area of the skin by moving the microcrystals of alumina over the area of the skin.

9. The method of claim 8, wherein the composition comprises 14 grams of alumina per ounce of cream.

10. A method comprising:
    applying to an area of skin a composition comprising a moisturizer and an effective amount of microcrystals of alumina; and
    removing an epidermal layer of skin over the area of skin by moving the composition over the area of skin with a vibrating instrument having a sponge disposed on the vibrating instrument.

* * * * *